(12) United States Patent
Aripin et al.

(10) Patent No.: US 8,569,382 B2
(45) Date of Patent: Oct. 29, 2013

(54) **ISOLATED COMPOUNDS FROM *PHALERIA MACROCARPA* AS ANTI-CANCER AGENTS**

(75) Inventors: Asep Aripin, Tangerang (ID); Poppy Firzani Arifin, Tangerang (ID); Raymond R. Tjandrawinata, Tangerang (ID)

(73) Assignee: PT. Dexa Medica, Sumatera Selatan (ID)

( * ) Notice: Subject to any disclaimer, the term of this patent is extended or adjusted under 35 U.S.C. 154(b) by 82 days.

(21) Appl. No.: 13/131,261

(22) PCT Filed: Nov. 26, 2009

(86) PCT No.: PCT/IB2009/055353
§ 371 (c)(1),
(2), (4) Date: Jun. 24, 2011

(87) PCT Pub. No.: WO2010/064172
PCT Pub. Date: Jun. 10, 2010

(65) Prior Publication Data
US 2011/0257112 A1    Oct. 20, 2011

(30) Foreign Application Priority Data
Dec. 2, 2008 (ID) .................... P00200800766

(51) Int. Cl.
*A01N 35/00* (2006.01)
*A61K 31/12* (2006.01)

(52) U.S. Cl.
USPC ........... 514/686; 514/675; 514/678; 514/679; 514/685

(58) Field of Classification Search
None
See application file for complete search history.

(56) References Cited

U.S. PATENT DOCUMENTS

2007/0203249 A1* 8/2007 Cerchietti ............. 514/673

OTHER PUBLICATIONS

Ferrari et al. Phytochemistry (2000), vol. 54, pp. 883-889.*
Matsuda et al. Biol. Pharm. Bull. (2001), vol. 24, pp. 586-587.*
Oshimi et al. J. Nat. Med. (2008), vol. 62, pp. 207-210.*
Nikaido et al. Journal of Medicinal Plant Research, Planta medica (1981), vol. 43, pp. 18-23.*

* cited by examiner

*Primary Examiner* — Patrick Lewis
(74) *Attorney, Agent, or Firm* — Neifeld IP Law, P.C.

(57) ABSTRACT

The invention concerns compounds DLBS1425E2.2 and DLBS1425F1 isolated and identified from the extract of the plant *Phaleria macrocarpa* (Scheff.) Boerl. The invention also relates to the use of said compounds, either as a single active compound or in combination, in a pharmaceutical dosage form that has anti-proliferative activity of cancer cells, and its use relating to female related diseases. Formula (I).

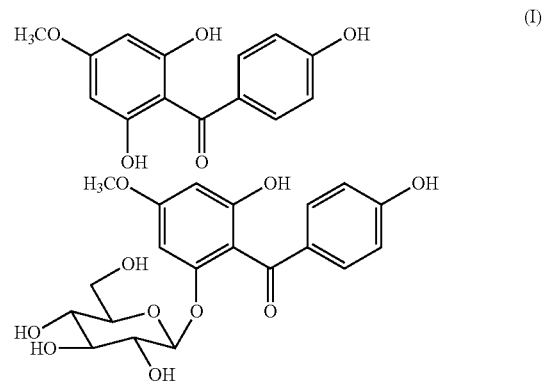

4 Claims, 8 Drawing Sheets

Keterangan:

| | | |
|---|---|---|
| M | : | Marker |
| Lane 1 | : | E2.2 50 microgram/ml |
| Lane 2 | : | E2.2 75 microgram/ml |
| Lane 3 | : | E2.2 100 microgram/ml |
| Lane 4 | : | Doxorubicin 10 microgram/ml |
| Lane 5 | : | Control |

ISOLATED COMPOUNDS FROM *PHALERIA MACROCARPA* AS ANTI-CANCER AGENTS

FIELD OF THE INVENTION

The present invention relates to compounds from *Phaleria macrocarpa* (Scheff.) Boerl. plant including preparation process of compound isolation and biological activities of such compounds. Two compounds have been isolated from *Phaleria macrocarpa* named DLBS1425E2.2 and DLBS1425F1. Both compounds show anti proliferation activity against MDA-MB-231 cancer cells. DLBS1425E2.2 compound also shows apoptosis inducer activity. Both compounds in accordance with the present invention can be applied in treatment of female related diseases or other gynecological diseases such as cancer, adenoma, cyst, related to breast, uterus, cervical, and ovary.

BACKGROUND OF THE INVENTION

Cancer is one of the most leading death causing diseases in Indonesia, since until now no effective treatment has been found, especially for late stage of cancer. Cancer is caused by neoplasia which is an abnormal proliferation of cells within a tissue or an organ, resulting in a mass known as a neoplasm. Tumor is a neoplasm that has formed a lump; while other type of neoplasm may not form a lump, for example cervical intraepithelial neoplasia, anal intraepithelial neoplasia, and leukemia. Neoplasm may be benign; however it can also be malignant. A benign neoplasm includes, for example, leiomyoma or uterine fibroids and melanocytic nevi or moles. A malignant neoplasm includes, for example, teratoma, also includes various kinds of cancer, including breast cancer.

One of the prevention and treatment method against cancer is by using herbal medicine. One of the plants that possess anti cancer properties is *Phaleria macrocarpa* (Scheff.) Boerl., a native plant of Papua that is widely known in Indonesia as "mahkota dewa".

In Indonesian patent application P00 2005 00077, it has been taught that the flavonoid extract of mahkota dewa was useful as anticancer based on its ability to reduce tyrosine kinase activity, its capacity as antioxidant, and its activity against HeLa cancer cells. Another Indonesian patent application P00 2008 00334 has taught that mahkota dewa extract was useful as an antineoplastic, antiinflammatory, and antiangiogenic agent. But in those patent applications, it has not been explained which compound is useful in such plant extract.

In the present invention, it will be learned about benzophenone compounds as major components which are isolated and identified from the fruits of mahkota dewa also their effects as anti proliferating agent shows by their potential in inhibiting cell growth and stimulating apoptosis which may induce cancer cell death.

BRIEF DESCRIPTION OF THE INVENTION

The objects and/or solutions which are taught from the present invention will be set forth in the preferred embodiments. The embodiments illustrated to serve the purpose of understanding the present invention, without limiting the possibilities of other embodiments which can be learned from the practice of the present invention. The objects and/or solutions which are taught in the present invention will be realized from the elements and combinations detailed in the claims herein.

To attain the object and/or solutions of the present invention, as explained in the embodiments and broadly described in this application, the first aspect of the present invention is directed to a pharmaceutical preparation which comprises: (1) *Phaleria macrocarpa* (Scheff.) Boerl. compound, for the purpose of the present invention it will be used herein namely DLBS1425E2.2 hereinafter abbreviated as E2.2, and (2) *Phaleria macrocarpa* (Scheff.) Boerl. compound, for the purpose of the present invention it will be used herein namely DLBS1425F1 hereinafter abbreviated as F1. Such E2.2 and F1 compounds as single active compound or in combination, in effective amount or dose are useful for cancer treatment or therapy. Pharmaceutical dosage forms according to the present invention may also contain excipients that are pharmaceutically acceptable.

The second aspect of the present invention is directed to a pharmaceutical preparation which contains E2.2 and F1 compounds which function as anti proliferation of cancer cells also female related diseases or other gynecological diseases such as cancer, adenoma, and cyst related to breast, uterus, cervical, and ovary.

The third aspect of the present invention is directed to E2.2 pure compound which has basic structure of benzophenone, diphenylmethanone, diphenylketone, or benzoylbenzene with 3 hidroxyl groups (—OH) substituted at carbon 2, 6, and 4'; a methoxy group (—OCH$_3$) substituted at carbon 4.

The fourth aspect of the present invention is directed to F1 pure compound that has basic structure of benzophenone, diphenylmethanone, diphenylketone, or benzoylbenzene with 2 hidroxyl groups (—OH) substituted at carbon 4' and 6; a methoxy group (—OCH$_3$) substituted at carbon 4, and a β-D-glycopyranoside substituted at carbon 2.

BRIEF DESCRIPTION OF THE DRAWINGS

The following drawings, which are incorporated in and constitute a part of the specification of the present application, illustrate one or several embodiments of the invention. The following drawings serve to explain the principles which are taught by the present invention.

FIG. 5 (*b*) shows an illustration of ion fragmentation from MS FAB F1 data.

FIG. 10 (*b*) shows a bar diagram indicating semiquantitatively BCl$_2$ RT-PCR products in MDA-MB-231 cells.

FIG. 11 (b) shows a bar diagram indicating semiquantitatively Bax RT-PCR products in MDA-MB-231 cells.

DETAILED DESCRIPTION OF THE INVENTION

The present invention will be discussed in details by giving examples without limiting the scope of the invention to the examples described.

E2.2 and F1 compounds according to the teaching of the present invention originally come from the fruits of *Phaleria macrocarpa* (Scheff.) Boerl. The fruits being used are ripe fruits of *Phaleria macrocarpa*. The plants of *Phaleria macrocarpa* grow in various locations inside and outside of Indonesia, preferably *Phaleria macrocarpa* which are planted at 10-1200 meters altitude in Java. It will be described herewith the preparation for extraction procedure of E2.2 and F1 compounds.

E2.2 and F1 compounds according to the present invention function as anti proliferation, apoptosis inducer, anti cancer and anti neoplasia which can be used as treatment toward cervical intraepithelial neoplasia, anal intraepithelial neoplasia, leukemia or other diseases caused by neoplasia, including leiomyoma also other female gynecological related diseases such as cancer, adenoma, cyst related to breast, uterus, cervical, and ovary.

A. Isolation Methods

1. First Method of E2.2 and F1 Compounds Preparation (Method 1)

Figure 1:
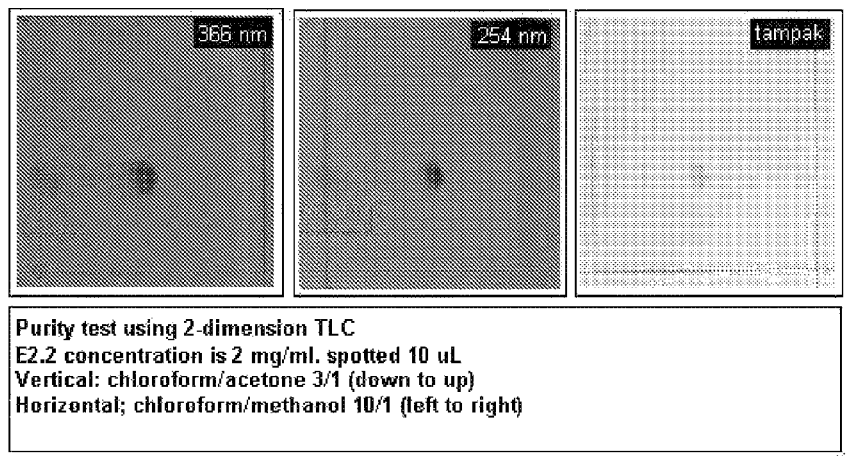
FIG. 1 shows a two-dimension diagram of thin layer chromatography (TLC) results of E2.2 purity test.

Single compound of E2.2 and F1 derived from ripe fruits of mahkota dewa by some process steps: alcohol extraction, fractionation by organic solvent or liquid-liquid extraction, preparative chromatography or purification, crystallization and identification.

a. Alcohol Extraction:

Plant materials which are identified as ripe fruits of mahkota dewa named DLBS14, were grinded, then extracted with alcohol solvent at a ratio in the range of 1:2 to 1:20 for certain incubation time with maximum 4 days at room temperature to 70° C. Undesired plant materials were separated as residue. Dry extract of this process was called DLBS1437.

b. Liquid-Liquid Extraction/LLE:

Certain amount of DLBS1437 were fractionated by LLE technique using mixture of organic solvent and water at a ratio in the range of 1:1 to 2:1 at room temperature, then were incubated maximum one night, thus it produced 2 layers. Upper layer, organic phase, was collected for the following process, while the remaining water fraction was discarded.

c. Purification:

To the organic phase, LLE products were fractionated with preparative chromatography column (stationary phase: silica gel; mobile phase: organic solvents) where E2.2 isolate compound was obtained from an E fraction which was purified by crystallization using chloroform solvent. An F1 compound was obtained from an F fraction which was purified by re-crystallization with ethanol-water.

d. Identification:

E2.2 compound physically is a yellow-orange crystal with melting point 173.1-174.7° C. TLC assay at $SiO_2$ gel media was eluted with chloroform/acetone solvent system 5/1 (v/v) migrated at Rf 0.32, analyzed with UV lamp at either long or short $\lambda$ produced positive results, while derivatization using 5% sulphate acid followed by heating produced bright orange color. See FIG. 1. Spectroscopy UV data showed 2 peaks, with maximum peak at 294.5 nm.

IR spectroscopy of E2.2 compound read peaks at 3288 (read as hydroxyl), 1731 (read as conjugated ketone C=O, middle), 1070 (read as C—O, strong), 1579, 1608 (read as C=C conjugated), 1400-1600 (read as C=C aromatic), 2858, 2913 (read as C—H aliphatic). IR spectroscopy data of E2.2 compound above showed absorbancies as indication of hydroxyl, carbonyl, 0-ether, conjugated carbon-carbon bonds, and hydrogen-carbon aliphatic groups.

Figure 2:
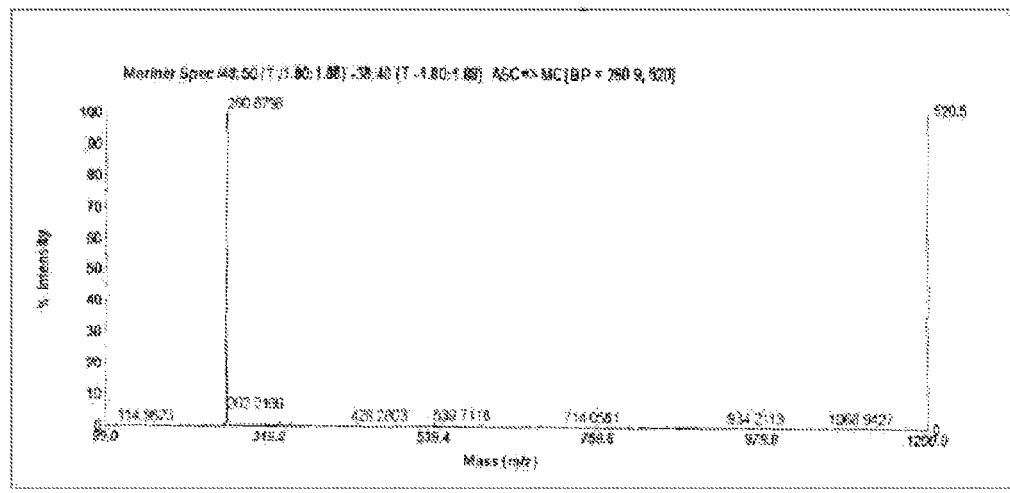
FIG. 2 shows an MS measurement result of E2.2 compound.

Based on NMR results, it was obtained proton NMR data which showed signals at chemical shift ($\delta$): 5.9 (s); 7.52 (d, JHz=8.55); 6.68 (d, JHz=8.55); 3.68 (s). Carbon NMR data showed carbon signals at chemical shift: 198.5; 165.6; 161.2; 161; 133; 132.8; 115.5; 108; 94.3; 55.5. Based on MS (mass spectroscopy) data E2.2 compound has a relative molecular mass 260.88 g/mol with formula $C_{14}H_{12}O_5$. MS data results are shown in FIG. 2.

Figure 3:
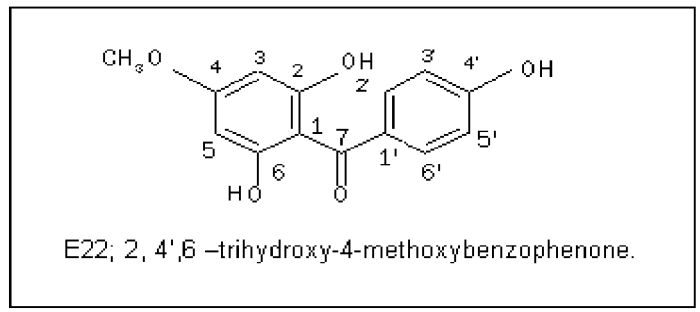
FIG. 3 shows an E2.2 compound structure.

From all spectroscopy data showed by E2.2 isolate compound directed to benzophenone group compound (or: diphenylmethanone, diphenylketone, benzoylbenzene). E2.2 compound structure is illustrated in FIG. 3. E2.2 compound is a compound of benzophenone group with 3 hydroxyl groups (—OH) substituted at carbon 2, 6, and 4'; methoxy group (—OCH$_3$) substituted at carbon 4. Therefore, chemical name (IUPAC) of E2.2 compound is 2,4',6-trihydroxy-4-methoxy-benzophenone.

Figure 4:
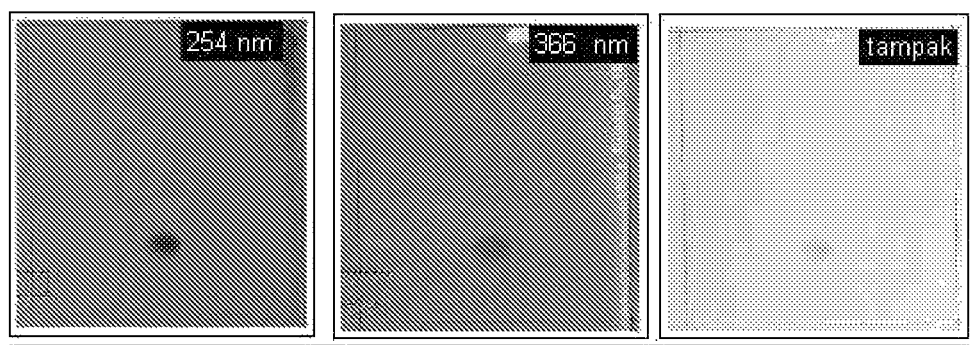
FIG. 4 shows a two-dimension diagram of TLC results of F1 purity test.

F1 compound physically is a white crystal solid with melting point 204.5-204.7° C. TLC assay in $SiO_2$ gel media eluted with chloroform/methanol/water solvent system 8/2/0.1 (v/v/v) migrated at Rf 0.35, analysis with UV lamp at either long or short $\lambda$ showed positive results, while derivatization with 5% sulphate acid followed by heating produced bright orange color with stronger intensity compared to E2.2 compound. See FIG. 4. UV spectroscopy data showed 2 peaks, with a maximum peak at 292.5 nm.

IR Spectroscopy data of F1 compound read peaks at 3363 (read as hydroxyl in aromatic), 3207 (read as hydroxyl in aliphatic, peak relative wide, because OH>1), 1651 (read as conjugated ketone C=O, middle), 1087 (read as C—O, strong), 1608 (read as conjugated C=C), 1400-1600 (read as C—C aromatic), 2970, 2920, 2872, 2821 (read as C—H aliphatic). IR spectroscopy data of F1 compound above showed absorbancies as indication of hydroxyl group (binding to C aromatic), hydroxyl group (binding to C aliphatic), carbonyl, O-ether, conjugated carbon bond, hydrogen-carbon aliphatic single bond, respectively. Different with IR spectroscopy data of E2.2 compound, hydroxyl group in F1 compound was detected more than one. This was showed by absorbance peak at 3207 that is not sharp. Four absorbancies for hydrogen-carbon aliphatic single bond also give information of C—H bond in other group binding to the main structure.

Figure 5A:
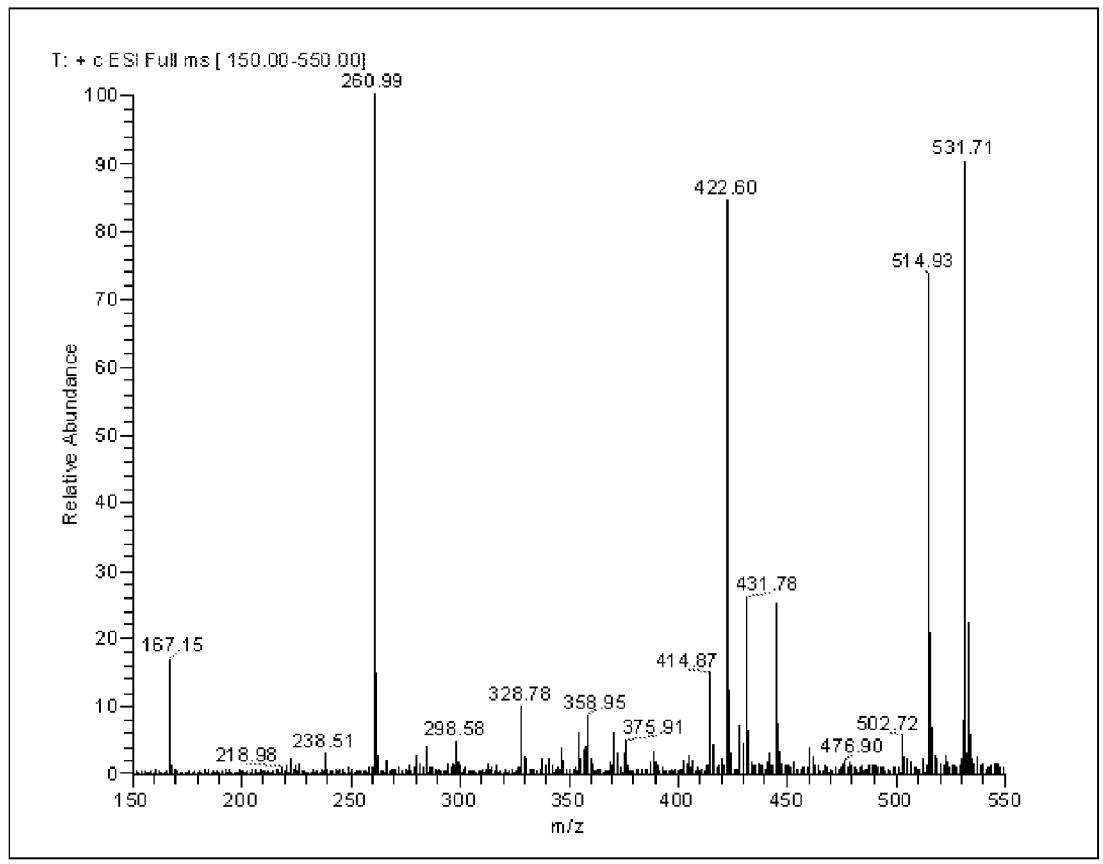
FIG. 5 (*a*) shows a measurement result of ions from MS FAB F1 data.
Figure 5B:
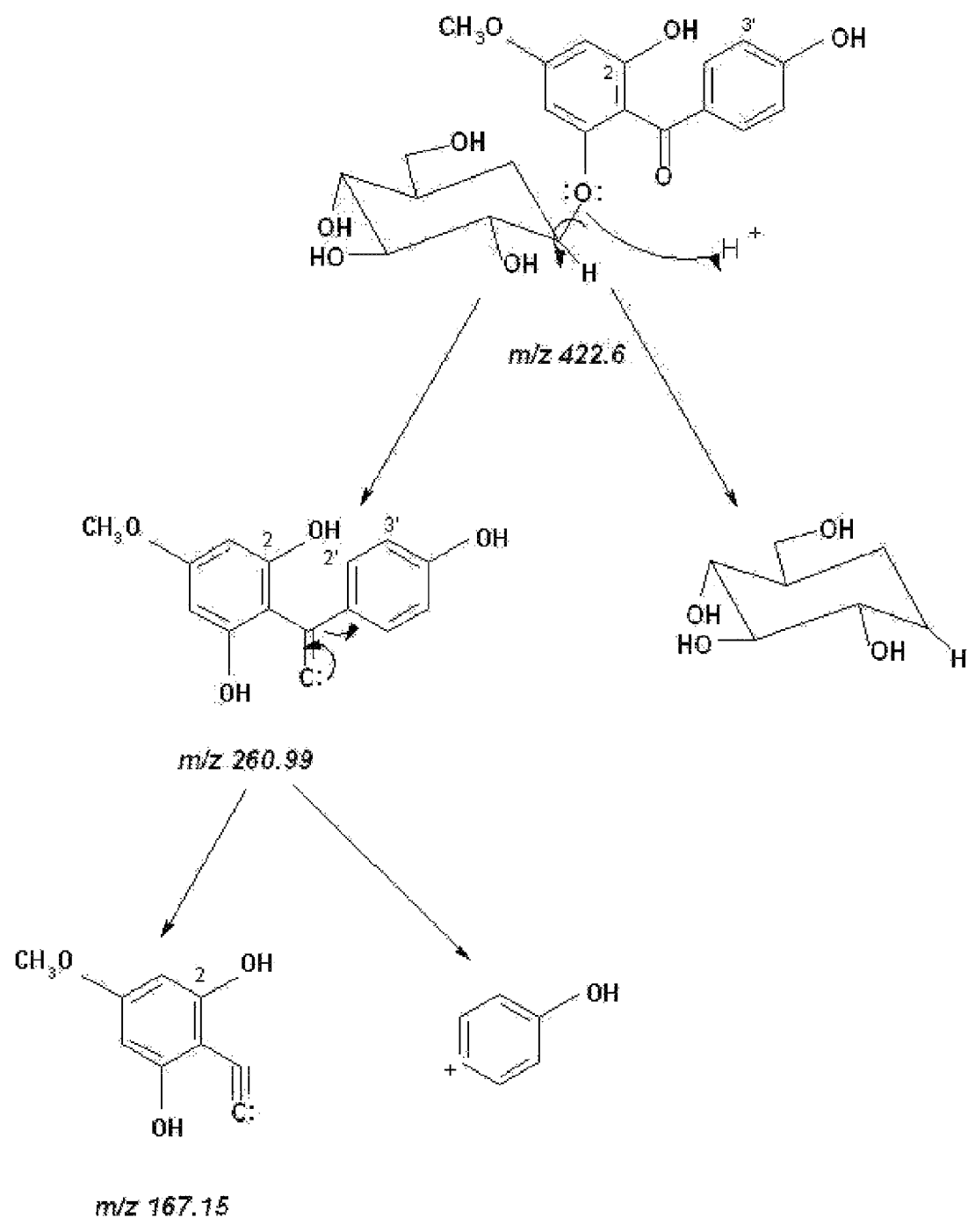

Based on NMR result, proton NMR data showed signals at chemical shift ($\delta$): 6.2; 6.4; 6.8; 7.7; $\delta$ 6.2 (1H, d, JHz=1.85); $\delta$ 6.4 (1H, d, JHz=1.85); $\delta$ 6.8 (2H, d, JHz=8.5) and $\delta$ 7.7 (2H, d, JHz=8.5); $\delta$ 3.8 (1H, s), $\delta$ 4.8 (2H, d, JHz=7.9). Carbon NMR data showed signals at chemical shift: $\delta$ 164.3; 164.10; 159.03; 158.51; 133.69; 131.84; 116.04; 111.77; 102.55; 96.80; 94.90; 78.41; 77.91; 4.83; 71.31; 62.65; 56.01 and $\delta$ 192.5 (C=O). Based on MS data F1 compound has relative molecular mass 422.6 g/mol with formula $C_{20}H_{22}O_{10}$. See FIG. 5a. This MS data supports the fact in F1 structure determination, with ions fragmentation illustration during FAB MS (Fast Atom Bombardment Mass Spectrometry) analysis process. F1 compound was analyzed using FAB MS machine, in the machine occurred H$^+$ atomic bombardment reaction to the F1 structure, thus it produced fragments that showed in peaks data at m/z 422.6; 260.99 and 167.15. Based on fragments value then it was reconstructed into the structure as shown in FIG. 5b. Such reconstruction result was in line with MS data analysis result.

Figure 6:
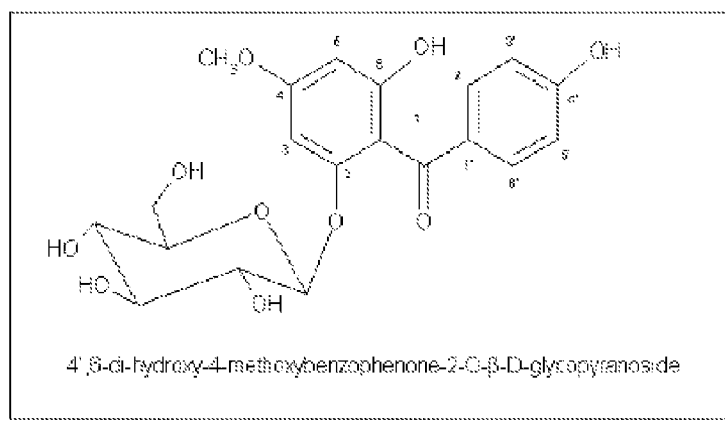
FIG. 6 shows an F1 compound structure.

From all spectroscopy data given by F1 isolate compound directed to benzophenone group compound (or: diphenylmethanone, diphenylketone, benzoylbenzene). F1 compound structure is illustrated at FIG. 6. F1 compound is a compound of benzophenone group compound with 2 hydroxyl groups (—OH) substituted at carbon 4' and 6; a methoxy group (—OCH$_3$) substituted at carbon 4, and β-D-glycopyranoside substituted at carbon 2. Therefore, a chemical name (IUPAC) of F1 compound is 4',6-di-hydroxy-4-methoxybenzophenone-2-O-β-D-glycopyranoside.

2. E2.2 and F1 Compounds Preparation (Method 2)

As an alternative, to obtain single isolate compound of E2.2 and F1 from ripe fruits of mahkota dewa, some steps are performed including conventional extraction process and supercritical CO$_2$ (SCFE-CO$_2$) extraction method, fractionation by liquid-liquid extraction using combination of organic solvents that is immiscible with water, preparative/purification column chromatography, crystallization, and identification.

a. Alcohol Extraction:

Alcohol extraction method in this Method 2 is similar to alcohol extraction in Method 1 from DLBS14 until DLBS1437 is produced.

b. Liquid-Liquid Extraction (LLE):

Liquid-liquid extraction method in this Method 2 is similar to liquid-liquid extraction in Method 1 until organic fractions are produced.

c. Purification

Dried organic fractions from LLE process then will be extracted selectively using liquid SCFE-CO$_2$ instrument, 5% co-solvent at condition: 2 hours of operation time, 50-60° C. of temperature. Simpler selective fractions are to be used in preparative chromatography column step. Based on chromatography orientation, an isolate was obtained from B-1 fraction similar to E2.2 isolate and it was later purified by recrystallization using mixture of alcohol and water solvents. An isolate was also obtained from B-2 fraction similar to F1 isolate compound and it was also purified later by recrystallization using mixture of alcohol and water solvents.

d. Identification:

Two isolate compounds obtained from SCFE-CO$_2$ extraction process were compared to E2.2 and F1 compounds based on the preparation according to Method 1. Identification result of SCFE-CO$_2$ extraction process showed that isolate compound from B-1 fraction was identical with E2.2 and isolate compound from B-2 fraction was identical with F1.

B. Anti Proliferation Effect of E2.2 and F1 Compound Against MDA-MB-231 Cancer Cells In this assay, the effect of E2.2 and F1 compounds as anti proliferation and E2.2 compound as apoptosis inducer against MDA-MB-231 cancer cells will be observed. MDA-MB-231 cells were cultured in supplemented medium cells, and then incubated at temperature 37° C., 5% CO$_2$.

1. Method a. Anti-Proliferation Assay of MDA-MB-231 Cancer Cells

This assay was performed in 96-well plates. Each well contained certain cancer cell density. After incubation for 24 hours, medium was changed into serum free medium, after that it was added with E2.2 compound sample as a single agent in various concentrations, so was with F1 compound. Cells were then re-incubated and after that the number of alive cells after treatment was determined by cell death determination assay. Absorbance value was read in microplate reader. After the absorbance value was converted with standard curve, the number of alive and death cells can be obtained.

Percentage of the number of alive cells in each treatment can be counted by counting the number of alive cells at wells that received treatment divided with the number of alive cells at healthy control and multiplied with 100%.

% The number of alive cells=$B/A\times100\%$

Notes: A is the number of alive cells at healthy control, and B is the number of alive cells that received treatment. IC50 value is a number showing a sample concentration that causes death as much as 50% in a population. Such value is obtained using BioStat statistical program.

b. DNA Fragmentation Analysis Method

Apoptosis is an active process of cell death marked with DNA chromosome cleavage, chromatin condensation, and also DNA fragmentation. In this experiment, it was observed the effect of E2.2 compound addition toward the formation of DNA fragmentation as one of apoptosis indicators. Cells were cultured in the plates. After incubation for 24 hours, it was added with E2.2 compound in various concentrations. DNA fragmentation determination was performed using DNA Apoptosis Ladder Kit. DNA fragmentation results were observed in electrophoresis gel, visualized using ethidium bromide.

c. Method of RNA Isolation and RT-PCR

BCl$_2$ and Bax genes are genes acting in apoptosis process. To identify BCl$_2$ and Bax mRNA expressions, RT-PCR (reverse-transcription PCR) was performed. MDA-MB-231 cancer cells were grown in plates and added with E2.2 compound samples as a single agent in various concentrations. Experiment condition was performed in serum free medium. RNA total was isolated from MDA-MB-231 cancer cells. RNA isolation products were quantified using spectrophotometer and visualized by agarose gel electrophoresis technique. The RNAs were then used in RT-PCR process using specific primers. RT-PCR process was performed in PCR machine with optimized condition. RT-PCR products were observed in electrophoresis gel which visualized using ethidium bromide.

Figure 7:
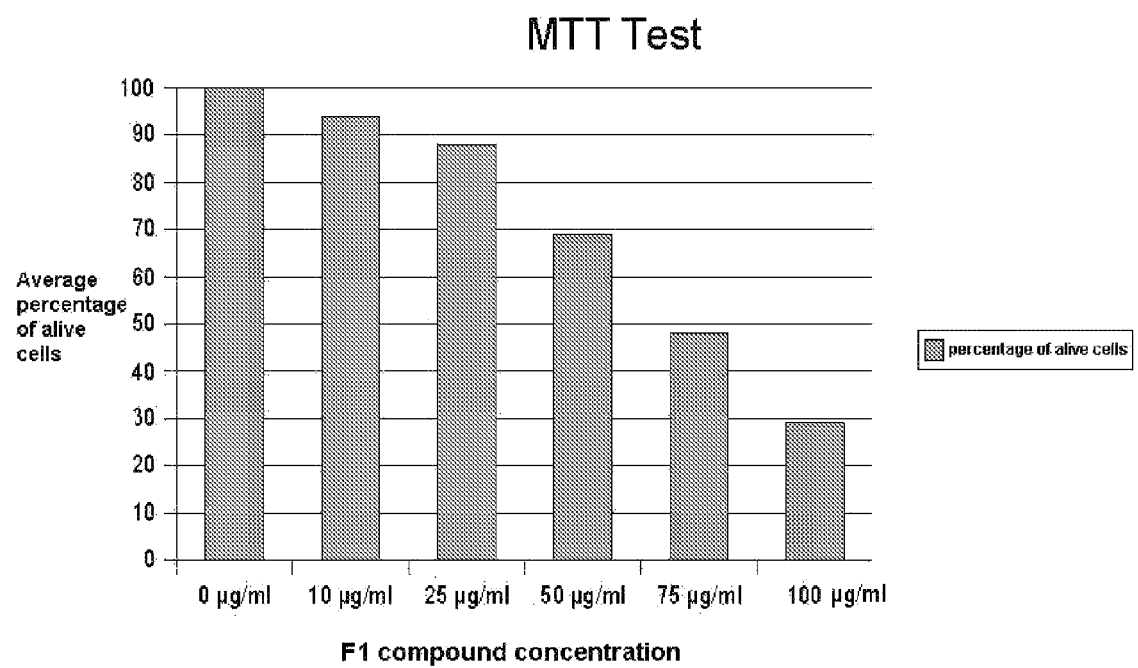
FIG. 7 shows a bar diagram indicating the effect of F1 compound against proliferation of MDA-MB-231 cancer cells.
Figure 8:
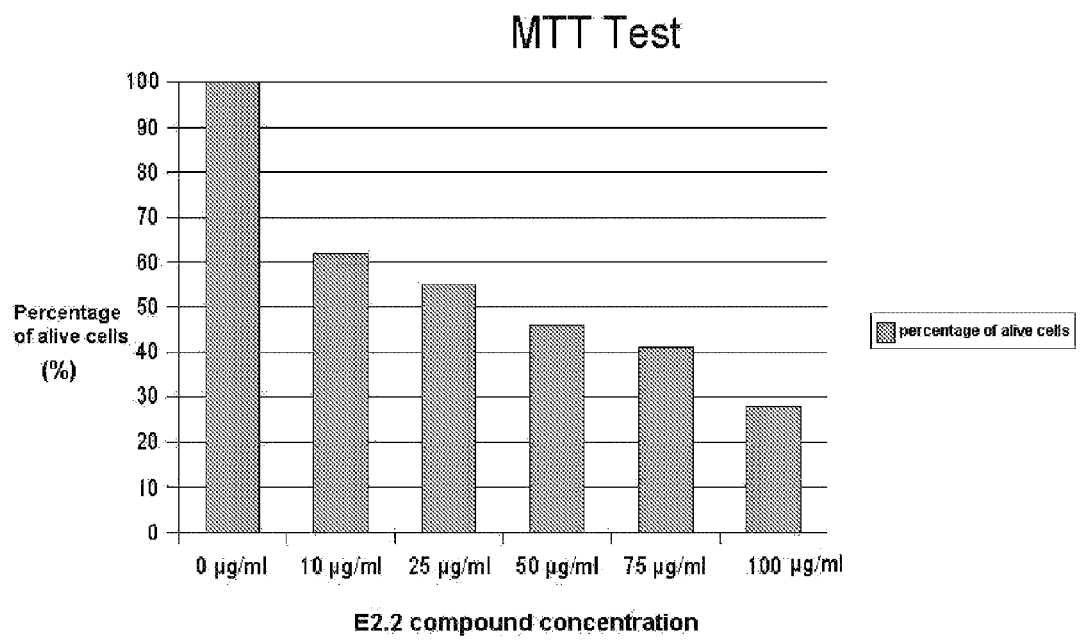
FIG. 8 shows a bar diagram indicating the effect of E2.2 against proliferation of MDA-MB-231 cancer cells.

2. Results a. Assay Results of the Effect of E2.2 and F1 Compounds Against Proliferation of MDA-MB-231 Cancer Cells Results showed that E2.2 and F1 compounds indicated anti proliferation effect in MDA-MB-231 cells. This was shown by significant decrease of percentage of alive cancer cell along with increase of the extract concentration. This was shown in FIG. 7 for F1 compound and FIG. 8 for E2.2 compound. Percentage data of alive cells were used in counting 1050 in MDA-MB-231 cells. IC50 value obtained from E2.2 compound in MTT result was 36.91 μg/mL while from F1 compound in MTT result was 65.80 μg/mL. Data was obtained using BioStat statistical program.

b. DNA Fragmentation Analysis Result

Figure 9:
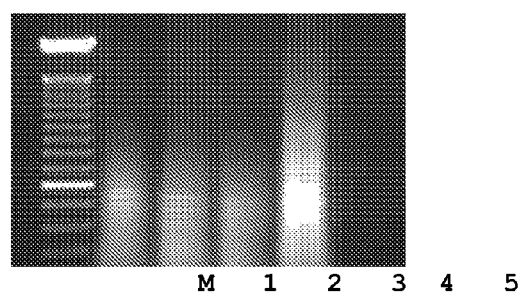
FIG. 9 shows a picture of electrophoresis results indicating formation of DNA fragmentation in MDA-MB-231 cells which are caused by E2.2 compound.

DNA fragments from samples obtained from MDA-MB-231 cells and treated with E2.2 compound in concentration 50, 75, and 100 μg/mL showed that E2.2 compound has an apoptosis inducer effect. One of apoptosis markers is the formation of DNA fragments as shown in FIG. 9.

c. BCl$_2$ and Bax RT-PCR Results

BCl$_2$ gene is one of oncogenes of BCL-2 family member which has an antiapoptotic property. BCL-2 family member is divided into two groups activities, proapoptosis and antiapoptosis. Cell sensitivity in stimulating apoptosis depends on the balance between proapoptotic and antiapoptotic proteins. If the proapoptotic proteins are abundant, then a cell will tend to undergo apoptosis, but if the antiapoptotic proteins are abundant then a cell will tend to resist against death.

Figure 10A:
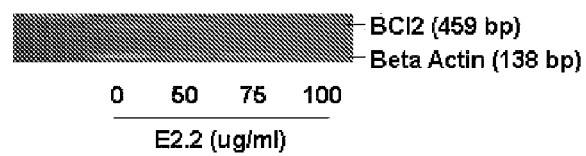
FIG. 10 (*a*) shows a picture of electrophoresis results of BCl$_2$ RT-PCR products.
Figure 10B:
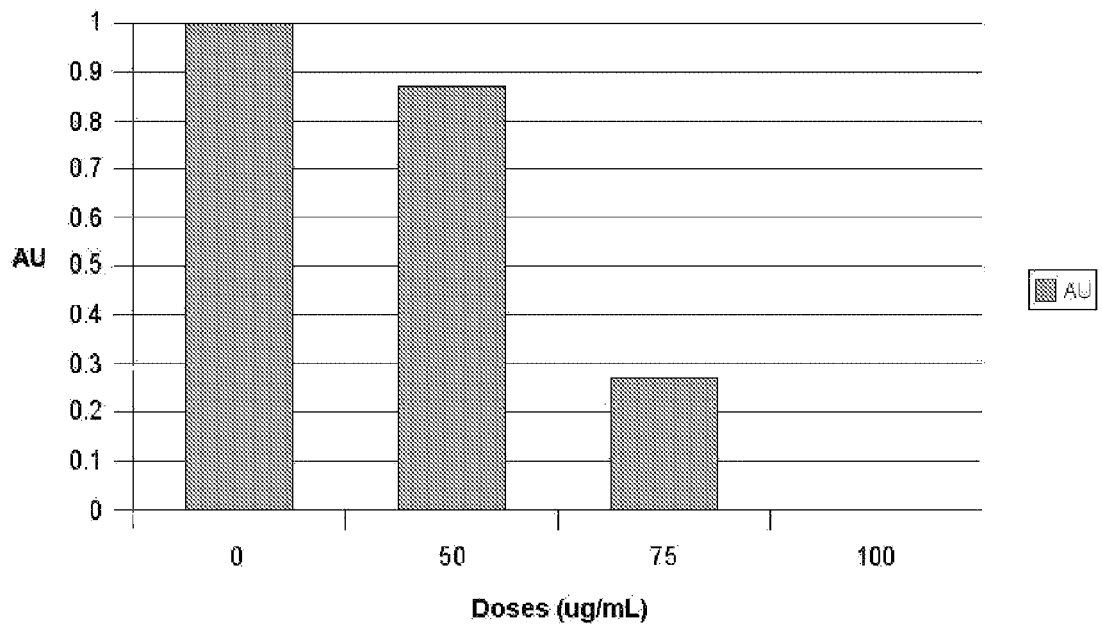

From the PCR results using $BCl_2$ specific primer, there was a downregulation of $BCl_2$ mRNA expression in MDA-MB-231 cells after treated with E2.2 compound. On the gel, it was observed that bands of $BCl_2$ gene amplification products were narrower by increasing the extract concentration administered. Quantitatively, the downregulation of $BCl_2$ in mRNA level is illustrated in FIGS. 10a and 1b.

Figure 11A:
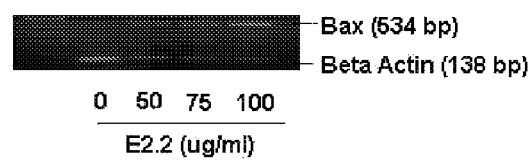
FIG. 11 (*a*) shows a picture of electrophoresis results of Bax RT-PCR products.
Figure 11B:
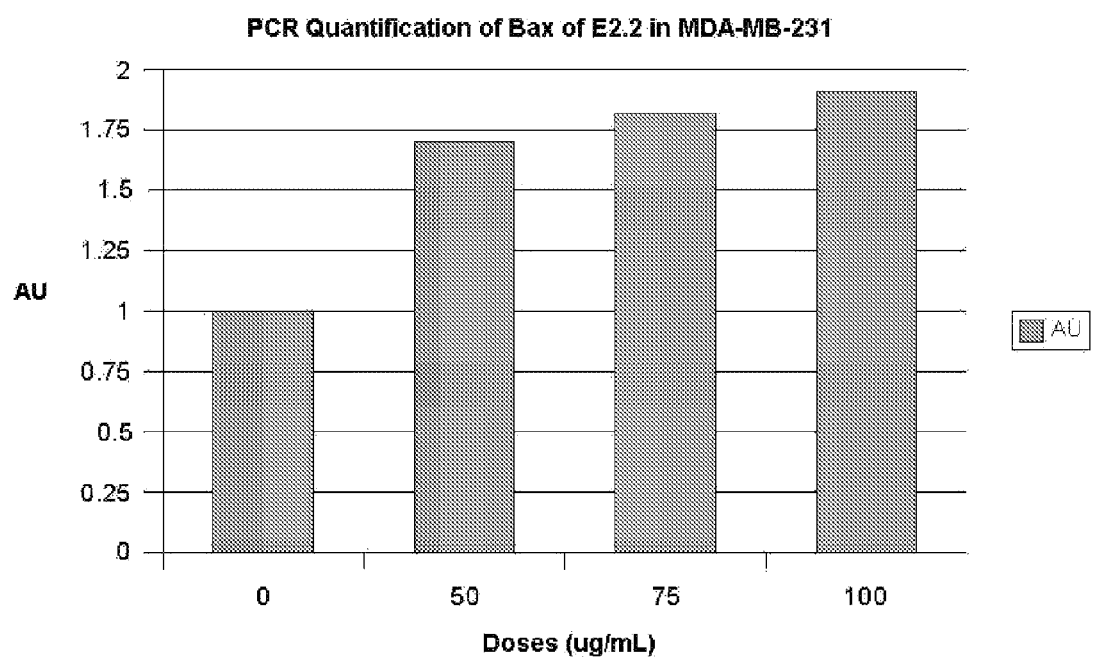

Contrary to that $BCl_2$, there was an upregulation of Bax in mRNA level in MDA-MB-231 cells. Analysis result showed that the higher E2.2 compound concentration, the denser the bands produced. See FIGS. 11a and 11b.

3. Discussion and Conclusion

Conclusion of the experiment results is that E2.2 and F1 compounds could induce inhibition of MDA-MB-231 breast cancer cell proliferation. IC50 value obtained from E2.2 compound was 36.91 µg/mL while from F1 compound was 65.80 µg/mL.

A material is called active having antiproliferation effect if it has IC50<100 µg/mL. Both compounds, E2.2 and F1 compounds, are benzophenone group which has cancer cell growth inhibition activity. The above results showed that E2.2 compound was more potent to inhibit cancer cell growth at lower dose compared to F1 compound. Therefore the apoptosis assay was more focused on E2.2 compound. The above data also showed that E2.2 and F1 compounds have potency as anti proliferation of MDA-MB-231 breast cancer cells.

Indication of apoptosis in MDA-MB-231 cells after administration of E2.2 compound is formation of DNA fragments, decrease of $Bcl_2$ mRNA expression and increase of Bax mRNA expression. Such results support deduction that E2.2 and F1 compounds are able to inhibit cancer cell proliferation and therefore it can be used as anti cancer. In addition, E2.2 and F1 compounds can be used to treat diseases caused by neoplasia (abnormal proliferation) also gynecological related diseases, such as cervical intraepithelial neoplasia, anal intraepithelial neoplasia, leukemia, leiomyoma, adenoma, and cyst related to breast, uterus, cervical, and ovary. Such results are also supported by the result of E2.2 compound which could stimulate apoptosis or cell death in cancer cells.

C. Pharmaceutical Dosage Forms and Nutraceutical

The present invention includes composition and pharmaceutical dosage forms that contain E2.2 and F1 compounds or one of them in an effective amount as active ingredient which is pharmaceutically acceptable and physiologically suitable.

In the process of making pharmaceutical composition according to the present invention, such E2.2 compound and/or F1 (are mixed with excipient(s), dissolved by excipient(s), or mixed in pharmaceutical carrier which can be made in the form of capsule, sachet, paper, also other materials or packagings. If pharmaceutically approved excipient is used as a solvent, the excipient can be in the form of solid, semi-solid or liquid (oral and injection), that reacts as a carrier or medium for the active substance. Thus, pharmaceutical composition according to this invention can be made in the form of pill, capsule, tablet, powder, sachet, solution, syrup, emulsion, suspension, effervescence tablets, gel, ointment, cream, and mouthwash, massage oil, suppository, or injection. Besides, pharmaceutical composition comprising E2.2 and F1, or one of them, according to this invention can also be made as supplement, vitamin, also food and beverage production.

Some examples of suitable excipients are microcrystalline cellulose, gelatin, lactose, dextrose, sucrose, sorbitol, mannitol, flour, calcium phosphate, calcium silicate, etc. Formulation according to this invention may also contain lubricant agent (such as talc, stearic magnesium, and mineral oil), wetting agent, preservative agent, sweetener and flavoring.

Composition according to this invention can also be made with formulation that cause active ingredient to be released directly, sustained, or controlled after the patient receives it using methods that have been applied in pharmaceutical industry. Tablet or pill according to this invention can be coated to extend the half life of the extract thus its frequency of use can be reduced.

Method of formulating this extract in a solid form, such as tablet, E2.2 and F1 compounds or one of them can be mixed with excipient(s) to form an initial formulation containing homogeneous mixture from the composition according to this invention. The initial formulation is a mixture contained the active ingredient of E2.2 and F1 compounds or one of them dispersed homogeneously so it can be properly distributed into the required dose in a dosage form, for example capsule, tablet, or pill.

Tablet or pill according to this invention can be added with a protection layer to reduce or cover bitter taste from the composition or active substance of E2.2 and F1 compounds or one of them.

E2.2 and F1 compounds or one of them in effective amount or dose according to this invention is the concentration or dose which the E2.2 and F1 compounds or one of them able to inhibit the growth of breast cancer cells and/or other gynecologic pathologic cells. The effective concentration depends on the physical condition of the patient, including weight, age, etc. and also depends on the type, size, and amount of cancer cells and other targeted pathologies.

This present invention also anticipates the therapeutic use of E2.2 and F1 compounds or one of them as prevention, concurrent, or after intrusive surgery to carry or take out neoplasm mass. The E2.2 and F1 compounds or one of them can be given directly to or around the location of neoplasm mass carried out from such intrusive surgery.

This present invention also anticipates the therapeutic use of E2.2 and F1 compounds or one of them that is used with or after the radiotherapy.

This present invention also anticipates the use of E2.2 and F1 compounds or one of them together with or additional to the composition of anti proliferation, apoptosis inducer, anti cancer, as well diseases caused by neoplasia and female related diseases or other gynecological diseases such as cancer, adenoma, and cyst related to breast, uterus, cervical, and ovary.

D. Application in Industry

E2.2 and F1 compounds or one of them and its pharmaceutical dosage forms can be produced in an industrial scale in production of extract, powder extract, and/or pharmaceutical dosage forms mainly for oral dosage form such as solid, semi-solid, or liquid that is used as anti proliferation, apoptosis inducer, anti cancer, female related diseases or other gynecological diseases such as cancer, adenoma, and cyst related to breast, uterus, cervical, and ovary.

The invention claimed is:
1. A method of treating cancer, comprising:
administering to a subject in need thereof an effective amount of E2.2 compound, wherein said amount is effective as an anti-proliferative agent.

2. A method of treating cancer, comprising:
   administering to a subject in need thereof an effective amount of E2.2 compound, wherein said amount is effective as an apoptosis inducer.

3. The method of claim 2 wherein said E2.2 compound downregulates $BCl_2$ mRNA expression.

4. The method of claim 2 wherein said E2.2 compound upregulates Bax mRNA expression.

* * * * *